US00PP16571P3

(12) United States Plant Patent
Weber et al.

(10) Patent No.: US PP16,571 P3
(45) Date of Patent: May 23, 2006

(54) STRAWBERRY PLANT NAMED 'CLANCY'

(50) Latin Name: *Fragaria×ananassa*
Varietal Denomination: Clancy

(75) Inventors: Courtney A. Weber, Geneva, NY (US); John C. Sanford, Livonia, NY (US); Kevin E. Maloney, Phelps, NY (US)

(73) Assignee: Cornell Research Foundation Inc., Ithaca, NY (US)

( * ) Notice: Subject to any disclaimer, the term of this patent is extended or adjusted under 35 U.S.C. 154(b) by 143 days.

(21) Appl. No.: 10/872,696

(22) Filed: Jun. 21, 2004

(65) Prior Publication Data

US 2005/0283869 P1 Dec. 22, 2005

(51) Int. Cl.
*A01H 5/00* (2006.01)

(52) U.S. Cl. ..... Plt./208
(58) Field of Classification Search ..... Plt./208, Plt./209
See application file for complete search history.

(56) References Cited

PUBLICATIONS

Varieties [online] [retrieved on Jan 26, 2005]. Retrieved from the Internet: <http://www.agraria.it/isf/attivit/fragola/ishs/varieties.htm#c>.*

* cited by examiner

*Primary Examiner*—Anne Marie Grunberg
*Assistant Examiner*—June Hwu
(74) *Attorney, Agent, or Firm*—Jondle & Associates P.C.

(57) ABSTRACT

This invention relates to a new and distinct June-bearing cultivar of strawberry plant named 'Clancy' primarily adapted to the growing conditions of west central New York and other regions of similar climate. The new cultivar is primarily characterized by strong vigor, large flowers, broader than long fruit, globose fruit shape, very large primary fruit, dark red fruit color, very firm fruit flesh, the upright attitude of pedicels and fruiting trusses, and late season fruit maturation.

3 Drawing Sheets

Genus and species: *Fragaria×ananassa* Duch.
Cultivar denomination: 'Clancy'.

SUMMARY OF THE INVENTION

The present invention relates to a new and distinct June-bearing (short day responsive) strawberry cultivar designated as 'Clancy'. The cultivar is botanically known as *Fragaria×ananassa* Duch. The new and distinct cultivar of strawberry originated from a hand-pollinated cross of United States Department of Agriculture selections MDUS4774 (not patented)×MDUS5199 (not patented) made in 1988 in Beltsville, Md. MDUS4774 is a June-bearing type producing large, very firm, conic shaped fruit that have a light red exterior, pale interior and ripen in mid-season. MDUS5199 is June-bearing with fruit that is dark red, firm fleshed, and globose shaped that ripens in the late season. Both parents of 'Clancy' are hybrids of the strawberry genus of the species *Fragaria×ananassa,* thus 'Clancy' is of the species *Fragaria×ananassa.* The seeds resulting from this controlled hybridization were germinated in a greenhouse in Beltsville during the winter of 1988–89 and shipped to the New York State Agricultural Experiment Station in Georgia, N.Y. for planting in the spring of 1989. The seedlings fruited in the summer of 1990 and one, designated NYUS304B, was selected for its attractive, large fruit, good flavor, late season ripening and firm flesh.

During 1990, the original plant selection was propagated asexually by stolons (runners) at Geneva, N.Y. and a test planting of ten plants was established. Subsequently, larger test plantings have been established with asexually multiplied plants at Geneva, N.Y. The new cultivar was then tested over the next several years in the fruiting fields at Geneva, N.Y. Further propagation in South Deerfield, Mass. was completed using tissue culture to produce disease free material for use in further testing. Tissue culture plants were used as mother plants for propagation from stolons. This propagation demonstrated that the combination of traits disclosed herein as characterizing the new cultivar are fixed and remain true to type through successive generations of asexual reproduction. All propagules of 'Clancy' have been observed to be true to type in that during all asexual multiplication, the vegetative and fruit characteristics of the original plant have been maintained. All plants planted from dormant crowns or rooted runner tips have fruited after one season of growth in the field.

Test plantings in various locations in New York, Pennsylvania, Ohio, Michigan, and Ontario, Canada have shown this cultivar to be widely adapted to differing soil and climatic conditions. The cultivar has shown cold hardiness typical to strawberries in a matted row system when covered with straw in the winter, which is standard procedure for this growing region. Fruit of the new cultivar ripens after the cultivar 'Jewel' (U.S. Plant Pat. No. 5,897) and similar to the varieties 'Cabot' (U.S. Plant Pat. Appl. No. 20030154530) and 'Eros' (not patented).

The new cultivar is primarily adapted to the climate and growing conditions of west central N.Y., the upper mid-western U.S., the mid-Atlantic states, and southeastern Canada and other regions of similar climate. These regions provide the necessary winter temperatures required for it to produce a strong, vigorous plant and to produce fruit in the summer harvest season from May through July, depending on location.

The following list of traits in combination define the new cultivar as a unique cultivar distinguishing it from other commercial varieties in the region:

upright growth habit, strong vigor;

dark green leaves with heavy leaf gloss and longer than broad leaflets;

large, broader than long fruit, globose fruit shape, pronounced cavity in primary fruit, dark red fruit and flesh color, and very firm flesh;

dense petiole pubescence;

relatively short, stiff pedicels and peduncles with frequent bracts that hold the fruit above the canopy;

late season production with moderate yields; and extended harvest season.

BRIEF DESCRIPTIONS OF THE PHOTOGRAPHS

The accompanying color photographs show typical specimens of the new cultivar at various stages of development as nearly true as it is possible to make in color reproductions. The depicted plant and plant parts were from the second harvest season, approximately 25 months after planting.

DETAILED BOTANICAL DESCRIPTION OF NEW CULTIVAR

Figure 1:
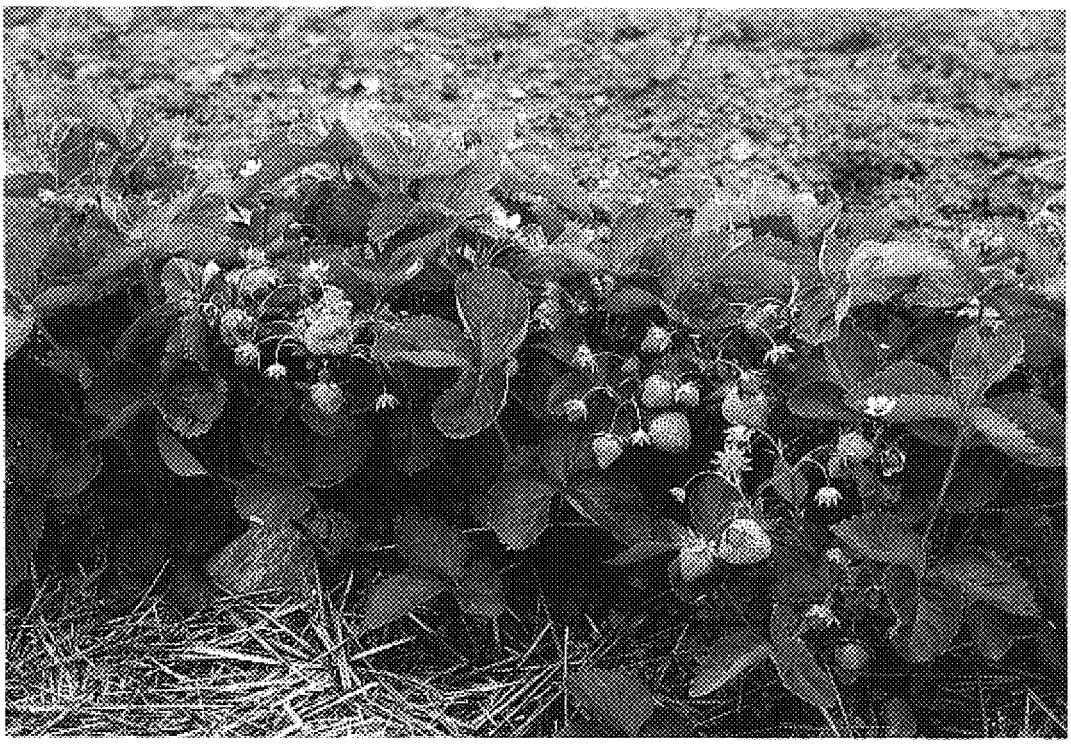
FIG. 1 shows typical fruiting truss of 'Clancy' demonstrating the projection of the fruit above the canopy on Jun. 20, 2003.
Figure 2:
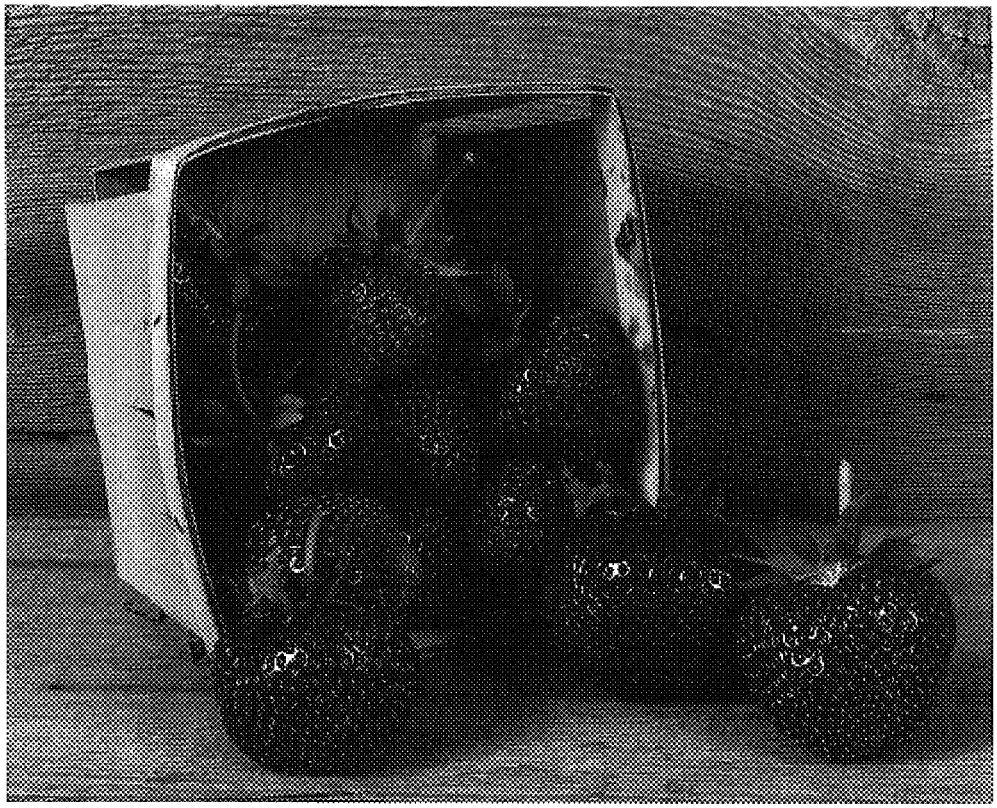
FIG. 2 shows typical fruit shape and uniformly of 'Clancy'.
Figure 3:
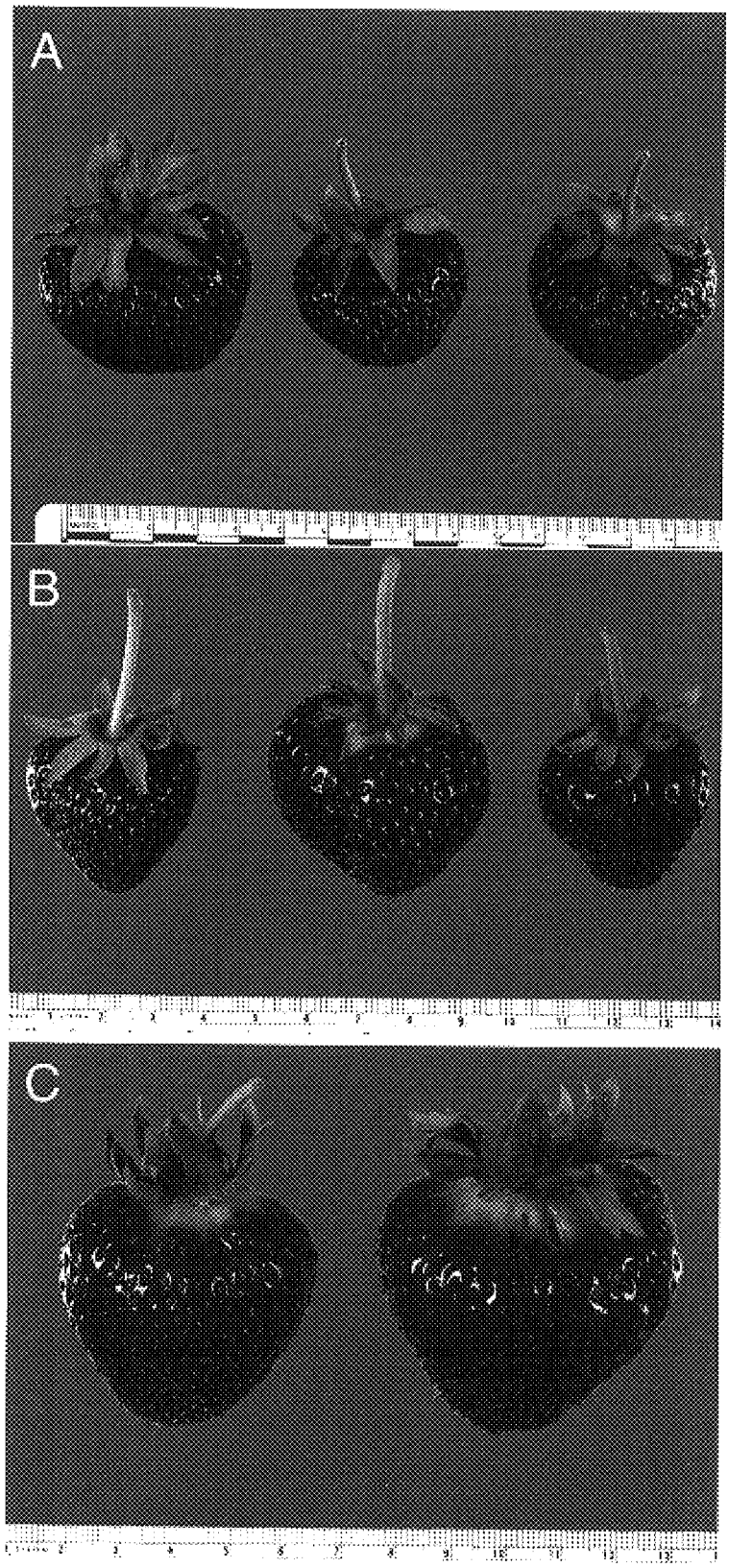
FIG. 3 shows typical external fruit characteristics of 'Clancy' (A), including calyx structure and fruit shape compared to 'Cabot' (B) and 'Jewel' (C) on Jun. 27, 2003.
Figure 4:
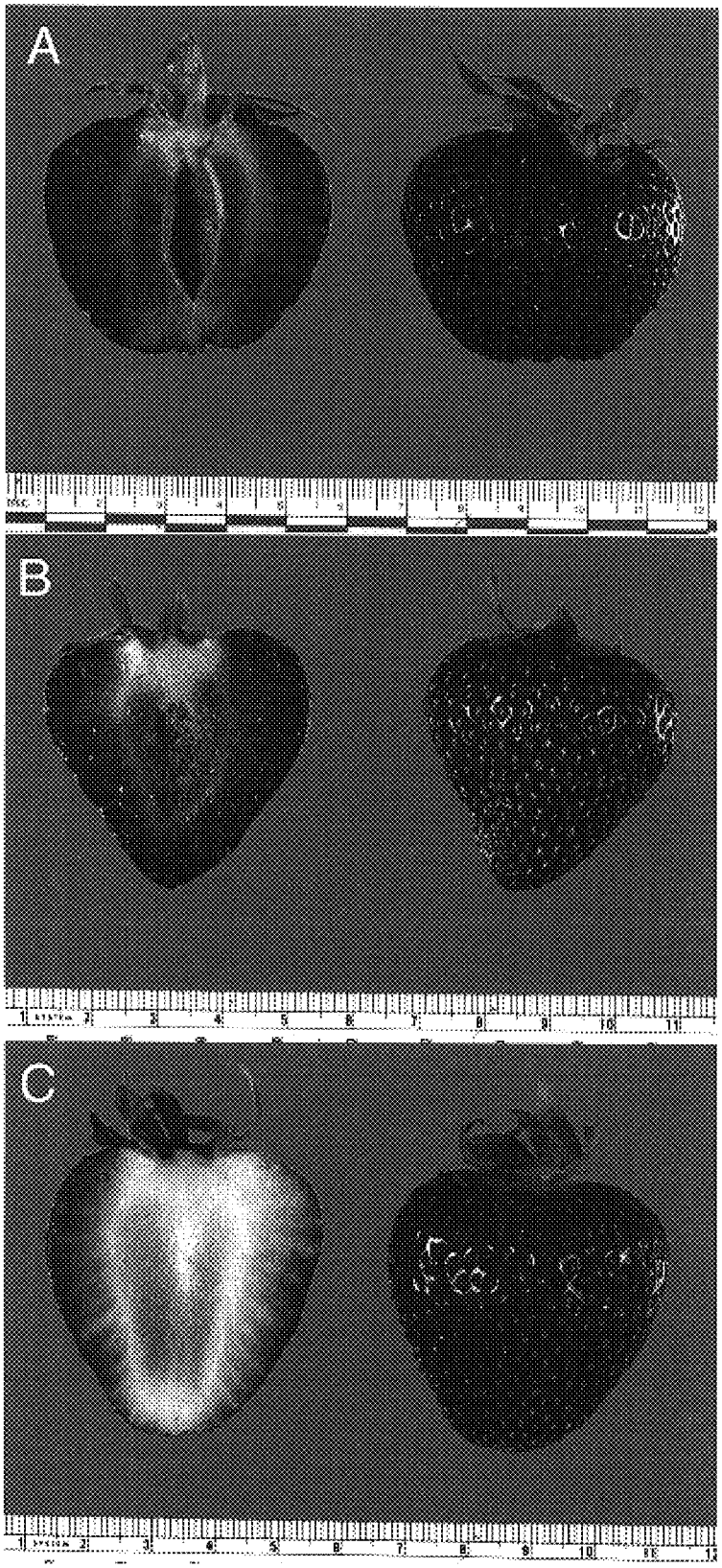
FIG. 4 shows typical internal fruit characteristics of 'Clancy' (A) compared to 'Cabot' (B) and 'Jewel' (C) on Jun. 27, 2003.

The following description of 'Clancy', unless otherwise noted, is based on observations taken during the 2003 growing season in Geneva, N.Y. These measurements and ratings were taken from plants produced in South Deerfield, Mass. and planted in May 2001. The age of the planting is approximately 25 months in its second harvest season. Yield observations and fruit quality characteristics are averaged from data collected during the 2002 and 2003 production seasons. The characteristics of the new cultivar may vary in detail, depending upon variations in environmental factors, such as temperature, rainfall, humidity and light intensity. 'Clancy' has not been observed under all possible environmental conditions. Color terminology follows The Royal Horticultural Society Colour Chart, London.

Comparative Fruit Characteristics:

'Clancy' fruit, fruit production and fruit quality characteristics. Fruit characteristics are taken from the second harvest season.

TABLE 1

Table 1 shows the 2002–2003 fruit yield and fruit size of 'Clancy' from Geneva, NY. Fruit was harvested in June 2002–2003. The plants of 'Clancy' and the other varieties were grown in a nursery in South Deerfield, MA and planted in May 2001 in Geneva, NY.

| Cultivar | 2002 | 2003 | Average | 2002 | 2003 | Average |
|---|---|---|---|---|---|---|
| | (kilograms per hectare) | | | (grams per berry) | | |
| 'Clancy' | 15,240 | 18,680 | 16,960 | 12.3 | 13.9 | 13.1 |
| 'Jewel' | 20,250 | 11,650 | 15,950 | 10.5 | 12.9 | 11.7 |
| 'Eros' | 22,340 | 6,680 | 14,510 | 12.6 | 10.9 | 11.8 |
| 'Cabot' | 29,070 | 17,380 | 23,230 | 17.7 | 15.5 | 16.6 |

TABLE 2

As shown in Table 2, comparisons of secondary fruit characteristics of 'Clancy' as compared with standard varieties from Geneva, NY Jun. 20, 2003. Measurements are given for mature fruit. Fruit width is measured across the widest part of the berry, typically across the shoulders.

| Characteristic | 'Clancy' | 'Cabot' | 'Eros' | 'Jewel' |
|---|---|---|---|---|
| RHS Exterior Color | Red 46A | Red 45A | Red 44B | Red 44A |
| Mature Fruit Length Mean (cm) | 3.07 | 4.28 | 3.55 | 3.46 |
| Mature Fruit Width Mean (cm) | 3.59 | 4.13 | 3.41 | 3.61 |
| Mature Fruit Length/ Width Ratio | 0.86 | 1.04 | 1.04 | 0.97 |
| No. Sepals/Berry | 11.9 | 12.6 | 12.3 | 12.4 |

TABLE 3

As shown in Table 3, comparisons of 2003 fruit quality characteristics, including flavor and soluble solids (% Brix), titratable acidity and juice pH of 'Clancy' are compared with standard varieties from Geneva, N.Y.

Flesh firmness (fresh) is an average penetration pressure using a Fruit Firmness Tester (QA Supplies, LLC, Norfolk, Va.) measured on fruit on the day of harvest with a 3 mm probe following manufacturer's instructions.

Flesh firmness (stored) is an average penetration pressure after 6 days of storage at 2° C. using a Fruit Firmness Tester (QA Supplies, LLC, Norfolk, Va.) taken with a 3 mm probe following manufacturer's instructions.

Fruit appearance (fresh) is based on a scale of 1–5 (5 being best) on the day of harvest.

Fruit appearance (stored) is based on a scale of 1–5 (5 being best) after 6 days of storage at 2° C.

Fruit gloss (fresh) is based on a scale of 1–5 (5 being best) on the day of harvest.

Fruit gloss (stored) is based on a scale of 1–5 (5 being best) after 6 days of storage at 2° C.

Flavor is based on a scale of 1–10 (10 being best) rated on day of harvest by a panel of tasters.

Soluble solids are estimated from % Brix with % Brix being an indirect measurement of the sugar content in the fruit. The measurements are averaged from three samples on three dates during the harvest season.

Titratable acidity is the percent of malic acid equivalents. The figures shown are the average of three samples on three dates during the harvest season.

Juice pH is the average of three samples on three dates during the harvest season.

| Characteristic | 'Clancy' | 'Cabot' | 'Eros' | 'Jewel' |
|---|---|---|---|---|
| Flesh firmness (fresh) (g pressure) | 209.0 | 166.7 | 135.0 | 145.3 |
| Flesh firmness (stored) (g pressure) | 196.7 | 146.7 | 130.0 | 141.7 |
| Fruit appearance (fresh) | 3.7 | 3.3 | 3.3 | 4.7 |
| Fruit appearance (stored) | 3.0 | 2.3 | 2.7 | 4.0 |
| Fruit gloss (fresh) | 4.7 | 4.3 | 4.0 | 5.0 |
| Fruit gloss (stored) | 3.7 | 3.0 | 2.7 | 4.3 |
| Flavor | 5.3 | 6.1 | 5.8 | 6.7 |
| Soluble solids | 9.0 | 9.0 | 9.8 | 7.8 |
| Titratable acidity | 1.01 | 1.02 | 0.85 | 1.18 |
| Juice pH | 3.54 | 3.53 | 3.73 | 3.42 |

Detailed fruit characteristics of 'Clancy':

*Ratio of length/width.* —Broader than long.

*Size.*—Large.

*Aroma.*—High.

*Predominant shape.*—Globose.

*Difference in shapes between primary and secondary fruit.*—Little.

*Band without achenes.*—Intermediate width.

*Color of mature fruit.*—Bright to dark red.

*Evenness of color.*—Even.

*Glossiness.*—Intermediate.

*Insertion of achenes.*—Level to slightly recessed from surface.

*Attitude of the calyx segments.*—Mostly flush to slightly reflexed.

*Calyx color.*—RHS 146C.

*Size of calyx in relation to fruit diameter.*—Generally smaller.

*Adherence of calyx (when fully ripe).*—Strong.

*Firmness of skin.*—Strong.

*Firmness of flesh.*—Very firm.

*Color of flesh.*—Light red with lightening toward center (orange-red 33A). Darkens when over ripe to red 53A.

*Distribution of red color of the flesh.*—Marginal through central with lighter inner area.

*Hollow center.*—Strongly expressed in primary fruit. Weakly expressed in other fruit orders.

*Seed color.*—Medium yellow-green to dark red (yellow-green 154B to red 45B).

*Time of flowering (50% of plants at first flower).*—Late.

*Time of ripening (50% of plants with first ripe fruit).*—Late.

*Type of bearing.*—Fully short day responsive.

Comparative plant characteristics:

TABLE 4

Table 4 shows a comparison of plant characteristics of 'Clancy' along with other standard varieties from Geneva, NY Jun. 20, 2003. Plant characteristics are taken from a fully mature, mid-season plant. Vigor and Canopy Density are rated on a scale of 1–9 (9 being more vigorous or dense) in mature, replicated plots.

| Characteristic | 'Clancy' | 'Cabot' | 'Eros' | 'Jewel' |
|---|---|---|---|---|
| Plant Height Mean (cm) | 26.1 | 21.7 | 24.5 | 27.3 |
| Vigor | 6.0 | 4.33 | 4.9 | 5.0 |
| Canopy Density | 6.0 | 4.33 | 5.4 | 7.0 |

Detailed Plant Characteristics of 'Clancy':

*Size.*—Medium.

*Habit.*—Upright.

*Density.*—Medium.

*Vigor.*—Medium.

*Average spread.*—28.8 cm.

Comparative Foliage Characteristics:

TABLE 5

Table 5 shows a comparison of leaf characteristics of 'Clancy', with standard varieties from Geneva, NY on Jun. 20, 2003. Foliage characteristics are taken from a fully mature tri-foliate during mid-season.

| Characteristic | 'Clancy' | 'Cabot' | 'Jewel' |
|---|---|---|---|
| RHS Color (upper surface) | Green 137A | Green 138A | Green 138A |
| RHS Color (upper surface) | Green 139D | Green 137D | Green 137D |
| Terminal Leaflet Length Mean (cm) | 10.3 | 8.3 | 7.5 |
| Terminal Leaflet Width Mean (cm) | 8.6 | 7.7 | 7.6 |
| Terminal Leaflet Length/Width Ratio | 1.20 | 1.08 | 0.99 |
| Petiole Length Mean (cm) | 15.9 | 16.3 | 19.9 |
| Serrations/Leaf | 30.2 | 24.4 | 18.3 |
| Stipule Length Mean (cm) | 3.3 | 3.3 | 3.0 |
| Stipule Width Mean (cm) | 0.8 | 0.56 | 0.8 |

Detailed foliage characteristics of 'Clancy':

*Color of upper surface.*—Dark green.

*Color of lower surface.*—Nearly gray green.

*Shape in cross section.*—Slightly concave.

*Interveinal blistering.*—Light.

*Glossiness.*—Moderate to high.

*Number of leaflets/leaf.*—Three.

*Terminal leaflet.*—Size — Large. Length/width ratio — Longer than broad. Shape of base — Cuneate. Shape serrations — Acute.

*Petiole.*—Color: closest to RHS 145B (yellow-green) with a slight RHS 180C (greyed-red) overtone on 50% of the petioles. Pubescence density — High. Stipule color — Light to medium green (yellow-green 144B). Stipule texture — Moderately pubescent. Anthocyanin coloration of stipule — High blush of red-purple 57A. Attitude of hairs — Slightly downward. Size of bract leaflets — Small. Frequency of bract leaflets — Occur on approximately 30% of the petioles.

Comparative Flower and Inflorescence Characteristics:

TABLE 6

Table 6 gives a comparison of inflorescence and secondary flower characteristics of 'Clancy' as compared with standard varieties from Geneva, NY on May 20, 2003. Inflorescence characteristics are taken from a fully mature plant during full bloom. Flower characteristics are taken from a secondary flower during mid-season at full maturity. The fruiting truss length is measured from the base of the primary peduncle where it attaches to the crown of the plant to the furthest berry.

| Characteristic | 'Clancy' | 'Cabot' | 'Jewel' |
|---|---|---|---|
| Fruiting Truss Length Mean (cm) | 22.5 | 20.3 | 20.9 |
| Corolla Diameter Mean (mm) | 37 | 35 | 31 |
| Calyx Diameter Mean (mm) | 37 | 39 | 34 |
| Petal Length Mean (mm) | 16 | 14 | 14 |
| Petal Width Mean (mm) | 14 | 13 | 13 |
| Petal Length/Width Ratio | 1.14 | 1.05 | 1.09 |
| Petals/Flower Mean) | 6.9 | 6.4 | 6.3 |

Detailed inflorescence characteristics of 'Clancy':

*Position relative to foliage.*—Above.

*Fruiting truss length.*—Short.

Detailed flower characteristics of 'Clancy':

*Color.*—RHS 155C (white).

*Size.*—Large.

*Size of calyx relative to corolla.*—Equal.

*Relative position of petals.*—Slight overlap of 10% when fully open.

*Petal length/width ratio.*—Longer than broad.

*Petal shape.*—Nearly round; elongated at attachment.

Pest reactions: It is known to be moderately resistant to the two-spotted spider mite and susceptible to aphid and flower thrips. It is also known to be moderately resistant to grey fund mold and resistant to powdery mildew. The susceptibility of the new cultivar to any of the virus complexes of N.Y. has not been determined.

COMPARISON WITH KNOWN VARIETIES

'Clancy' is distinguished from its parents, MDUS4774 and MDUS5199 by having larger fruit with a firmer texture. It is more upright in habit than MDUS4774 with more stout fruiting trusses than both of its parents. The fruit is darker red than that of MDUS5199. The fruiting season is earlier than MDUS5199 and later than MDUS4774.

The varieties which are believed to most closely resemble 'Clancy' are 'Jewel' (U.S. Plant Pat. No. 5,897), 'Cabot' (U.S. Plant Pat. Appl. No. 20030154530), and 'Eros' (not patented).

When compared to similar cultivar 'Jewel', 'Clancy' differs by the following characteristics. The plant of 'Clancy' is shorter with more vigor and a less dense canopy. The leaflets are longer and somewhat broader and more conic in shape. The fruit of 'Clancy' is larger than that of 'Jewel' and the fruit skin and flesh color of 'Clancy' is darker red than that of 'Jewel'. The yield of 'Clancy' is greater than that of 'Jewel'. The fruit of 'Clancy' is firmer than that of 'Jewel' with less glossy skin. The fruit of 'Clancy' has higher soluble solids (% Brix) and lower titratable acids than that of 'Jewel' with higher juice pH. The calyx of 'Clancy' is showier, larger and more reflexed than that of 'Jewel'. The harvest season of 'Clancy' is later than that of 'Jewel' and more extended.

When compared to similar cultivar 'Cabot', 'Clancy' differs by the following combination of characteristics. The plant of 'Clancy' is taller and more vigorous compared to 'Cabot' with a denser canopy. The leaflets are longer and narrower, being more conic in shape with less interveinal leaf blistering. The length to width ratio of the terminal leaflet is much longer than broad compared to slightly longer than broad for 'Cabot'. The fruit of 'Clancy' is smaller in size, with darker red skin and flesh color than 'Cabot'. The fruit of 'Clancy' is firmer with glossier skin than 'Cabot'. The difference in shape between primary and secondary fruit is greater in 'Cabot' than 'Clancy'. The flowering trusses are longer with slightly fewer flowers than 'Cabot'. The flowers of 'Clancy' are larger in diameter than the flowers of 'Cabot' with petals that are longer than wide compared to equally long and wide in 'Cabot'. The calyx of 'Clancy' is smaller and less showy than that of 'Cabot'.

When compared with similar cultivar 'Eros', 'Clancy' differs by the following combination of characteristics. The plant of 'Clancy' is more vigorous with a taller, more upright habit and thicker canopy compared to 'Eros'. The fruit of 'Clancy' is larger in size, darker in color with better overall flavor than 'Eros'. The fruit of 'Clancy' is more globose being equally broad and long compared to 'Eros' which is more conic shaped. The calyx segments are slightly reflexed in 'Clancy' compared to flush with the fruit in 'Eros'. The fruiting trusses of 'Clancy' are longer in overall length than 'Eros' and more upright in habit, holding the fruit off the ground. The fruit of 'Clancy' has lower soluble solids, higher titratable acidity than that of 'Eros' with a lower juice pH.

We claim:

1. A new and distinct cultivar of strawberry plant named 'Clancy' substantially as herein described and illustrated by the characteristics set forth above.

* * * * *